United States Patent [19]

Chen et al.

[11] 4,215,048

[45] Jul. 29, 1980

[54] TOTAL SYNTHESIS OF (1RS, 4SR, 5RS)-4-(4,8-DIMETHYL-5-HYDROXY-7-NONENYL)-4-METHYL-3,8-DIOXABICYCLO[3.2.1]OCTANE-1-ACETIC ACID

[75] Inventors: Robert H. K. Chen, Belle Mead; Zoltan G. Hajos, Princeton, both of N.J.

[73] Assignee: Ortho Pharmaceutical Corporation, Raritan, N.J.

[21] Appl. No.: 40,345

[22] Filed: May 18, 1979

[51] Int. Cl.$^2$ .......................................... C07D 319/00
[52] U.S. Cl. .............................. 260/340.6; 260/343.6; 260/347.8; 260/348.25; 560/205; 568/840
[58] Field of Search .......................... 260/340.6, 343.6

[56] References Cited

U.S. PATENT DOCUMENTS

| | | | |
|---|---|---|---|
| 2,957,009 | 10/1960 | Holmquist et al. | 260/343.6 X |
| 4,011,177 | 3/1977 | Ansari et al. | 260/343.6 X |
| 4,102,895 | 7/1978 | Kanoja et al. | 260/340.6 |

OTHER PUBLICATIONS

Chem. Abstracts, 86:4902a.

*Primary Examiner*—Ethel G. Love
*Attorney, Agent, or Firm*—Benjamin F. Lambert

[57] ABSTRACT

A method for the total synthesis of (1RS,4SR,5RS)-4-(4,8-dimethyl-5-hydroxy-7-nonenyl)-4-methyl-3,8-dioxabicyclo[3.2.1]octane-1-acetic acid is described. The compound is active as a utero-evacuant agent.

12 Claims, No Drawings

TOTAL SYNTHESIS OF (1RS, 4SR, 5RS)-4-(4,8-DIMETHYL-5-HYDROXY-7-NONENYL)-4-METHYL-3,8-DIOXABICYCLO[3.2.1]OCTANE-1-ACETIC ACID

The present invention relates to a method for the total synthesis of (1RS,4SR,5RS)-4-(4,8-dimethyl-5-hydroxy-7-nonenyl)-4-methyl-3,8-dioxabicyclo[3.2.1]octane-1-acetic acid. The compound and its preparation from the naturally occurring compound known as zoapatanol are described in U.S. Patent No. 4,102,895 and has the following structure:

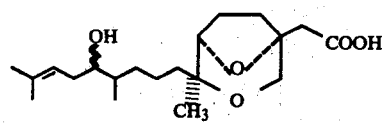

The bicyclic compound is active as a utero-evacuant agent.

The synthesis is comprised of several steps which are summarized in the following schematic diagram:

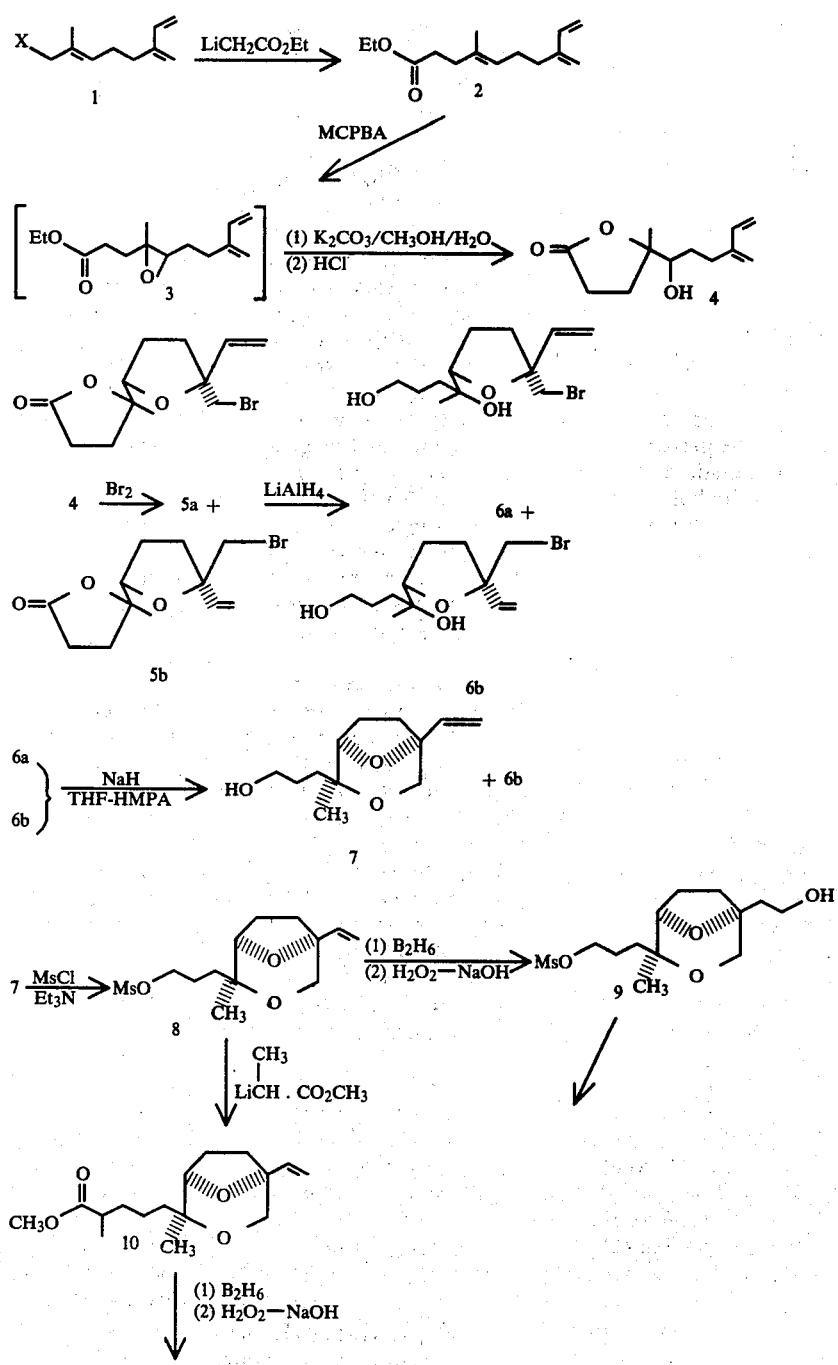

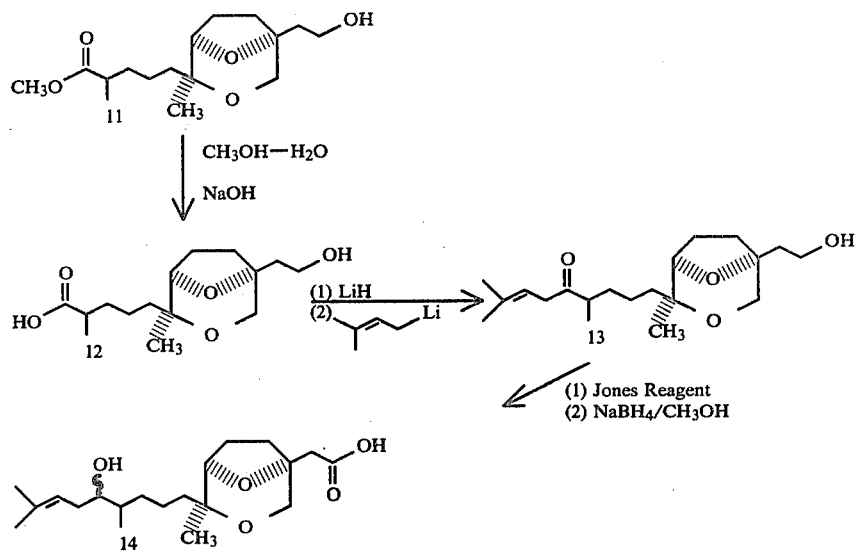

wherein X is chloro or bromo. MCPBA is m-chloroperbenzoic acid and MsCl is mesyl chloride.

As can be seen from the diagram, the first step in the synthesis involves the transformation of the triene (1) into the triene ester (2) by reaction with ethyl 2-lithioacetate (generated from ethyl acetate and lithium diisopropylamide). The reaction can be carried out at a temperature between −80°–0° C. in a suitable solvent such as tetrahydrofuran or dioxane. The preferred temperature is about −78° C. Alternatively, the triene ester (2) can be prepared by addition of 2-propenyl magnesium bromide to 4-methylene-5-hexenal to yield a secondary alcohol which is converted to the triene ester by treatment with an excess of triethyl orthoacetate. The reaction is preferably carried out in the presence of propionic acid as a catalyst and at a temperature of about 120°–140° C. in an inert atmosphere such as nitrogen, for example. The preferred temperature is about 130° C.

Epoxidation of the triene ester (2) with about one equivalent of m-chloroperbenzoic acid gives a crude monoepoxide which is used as such in the next two steps. The reaction is carried out in a solvent such as methylene chloride or chloroform at a temperature between about −10°–25° C. and preferably about 0° C. The crude epoxide is first hydrolyzed in a basic medium and then acidified with acid to afford the γ-lactone (4). As the basic medium, potassium carbonate, sodium hydroxide or sodium bicarbonate in a methanol-water solvent can be employed. Examples of acids which can be employed include hydrochloric acid and sulfuric acid. The crude lactone is purified by techniques known to those skilled in the art such as, for example, column chromatography.

The lactone (4) is then treated with bromine (about 1 equivalent) in a suitable solvent such as methylene chloride at a temperature of about −10°–20° C., and preferably about 0° C., to give a mixture of primary epimeric bromides [(5a) and (5b)] with simultaneous formation of a tetrahydrofuran ring. The mixture of lactones is treated with lithium aluminum hydride (about 1 equivalent) in a suitable solvent such as ether to give the corresponding bromo diols [(6a) and (6b)]. The reaction is preferably carried out in a suitable solvent such as methylene chloride at a temperature of about 0° C. Cyclization of the mixture of bromo diols [(6a) and (6b)] with about two equivalents of sodium hydride in a solvent mixture such as, for example, hexamethylphosphoramide-tetrahydrofuran or dimethylformamide-tetrahydrofuran at a temperature of about 50°–70° C., and preferably about 60° C., gives the primary alcohol (7). The alcohol (7) is purified by techniques known to those skilled in the art such as chromatography over an adsorbent material such as florisil, alumina or silica gel.

Treatment of the alcohol (7) with methanesulfonyl chloride in a suitable solvent such as methylene chloride in the presence of a base such as triethylamine affords the corresponding mesylate (8). The olefinic mesylate (8) is hydroborated with an excess of diborane in a suitable solvent such as tetrahydrofuran at a temperature between 0°–25° C. followed by oxidation with hydrogen peroxide in the presence of an aqueous base such as sodium hydroxide to afford a primary alcohol (9). The alcohol is then converted to the methyl ester (11) by reaction with methyl-2-lithio-propionate (generated from methyl propionate and lithium diisopropylamide) in a suitable solvent such as tetrahydrofuran at a temperature between −78°–25° C. Alternatively, the methyl ester (11) is prepared by reacting the mesylate (8) with methyl 2-lithio-propionate to form the corresponding ester (11) which is then hydroborated with diborane in a suitable solvent such as tetrahydrofuran followed by oxidation with hydrogen peroxide in the presence of aqueous alkali.

The ester (11) is then hydrolyzed in a basic medium such as sodium hydroxide in methanol-water and acidified with an inorganic acid such as, for example, concentrated hydrochloric acid to give the corresponding acid (12). Treatment of the acid (12) in ether with lithium hydride followed by reaction with 3-methyl-2-butenyl lithium gives the corresponding ketone (13). The ketone is purified by techniques known to those skilled in the art such as, for example, chromatography over an adsorbent material such as florisil, silica gel or alumina. The keto-alcohol (13) is then oxidized with a suitable oxidizing agent such as chromium trioxide-sulfuric acid (Jones reagent) in a solvent such as acetone to give a keto-acid which is converted without purification to (1RS,4SR,5RS)-4-(4,8-dimethyl-5-hydroxy-7-nonenyl)-4-methyl-3,8-dioxabicyclo[3.2.1]octane-1-acetic acid (14) by treatment with sodium borohydride or sodium cyanoborohydride in a suitable solvent such as methanol, ethanol or isopropanol. The reaction is carried out at a temperature between 0° C. and room temperature. The preferred reaction temperature is about 0° C.

The starting material employed in the synthesis of the dioxabicyclo compound, 1-bromo-2-methyl-6-methylene-2,7-octadiene is prepared according to the method of M. von P. Göpfert and R. Beck, Helv. Chim. Acta., 50, 2446 (1967).

The following examples describe the invention in greater particularity and are intended to be a way of illustrating but not limiting the invention.

EXAMPLE 1

Ethyl 4-methyl-8-methylene-(E)-4,9-decadienoate (2)

A. Lithium diisopropylamide (15 mM) is generated from n-butyl lithium and diisopropylamine in tetrahydrofuran (100 ml) in the usual manner. Ethyl acetate (1.3 g, 14.6 mM) is added to this reagent at −78° C. under nitrogen and the mixture is stirred for two hours. A solution of 1-chloro-2-methyl-6-methylene-2(E)-7-octadiene (2.5 g, 14.6 mM) in tetrahydrofuran (3 ml) is added dropwise during a ten minute period. The resultant mixture is stirred for two hours and then allowed to warm to 0° C., after which ice-water is added (50 ml). The aqueous phase is washed with brine (100 ml), water (2×100 ml) and then dried (Na$_2$SO$_4$). The solvent is removed in vacuo to give a crude product (2.9 g). This material is further purified by column chromatography on silica gel (50 g) with 10% ether in petroleum to give ethyl 4-methyl-8-methylene-(E)-4,9-decadienoate (2.1 g, 70%) as a colorless liquid.

IR (neat) 1738 and 1595 cm$^{-1}$

NMR (CDCl$_3$) δ 1.23 (t, J=7 Hz, 3H, C$\underline{H}_3$CH$_2$O—), 1.63 (bs, 3H,

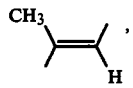

4.10 (q, J=7 Hz, 2H, CH$_3$C$\underline{H}_2$—O—), 4.87–6.57 (m, 6H, olefinic protons)

B. A mixture of 2-methyl-6-methylene-1,7-octadien-3-ol (34 g, 0.224 M), triethyl orthoacetate (80 g, 0.5 M) and propionic acid (1 ml) is heated at 135° C. (bath temperature) under nitrogen for four hours. The resulting mixture is cooled to room temperature and treated with pyridine (1 ml). Most of the excess reagent is removed in vacuo (high vacuum pump) and the residue is purified by column chromatography on silica gel (300 g) with 5% ether in petroleum ether, to give ethyl 4-methyl-8-methylene-(E)-4,9-decadienoate (35 g, 70%) as a colorless liquid.

EXAMPLE 2

2-Methyl-6-methylene-1,7-octadien-3-ol

2-Propenyl magnesium bromide is prepared under nitrogen from 2-bromopropene (50 g, 0.417 M) and magnesium (12 g, 0.5 M) in tetrahydrofuran (150 ml) in the usual manner. To this reagent, a solution of 4-methylene-5-hexenal (62 g, 0.564 M) in tetrahydrofuran (100 ml) is slowly added during a two hour period at 0° C. After the addition is complete, the mixture is allowed to warm to room temperature and then stirred overnight. The resulting mixture is poured into cold saturated ammonium chloride solution (500 ml) and the aqueous layer is extracted with ether (3×500 ml). The combined organic layers are dried (Na$_2$SO$_4$) and the solvent is removed in vacuo. The residue (56.5 g) is purified by column chromatography on silica gel (350 g) with 25% ether in petroleum ether to give 2-methyl-6-methylene-1,7-octadien-3-ol (32 g, 51%) as a colorless liquid.

IR (neat) 3430 cm$^{-1}$

NMR (CDCl$_3$) δ 4.08 (t, J=6 Hz, 1H,

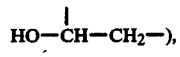

4.78–6.63 (m, 7H, olefinic protons)

EXAMPLE 3

2-(1-Hydroxy-4-methylene-5-hexenyl)-2-methyl-5-oxotetrahydrofuran (4)

m-Chloroperbenzoic acid (36 g, 0.175 M) is added in five portions to a mixture of ethyl 4-methyl-8-methylene-(E)-4,9-decadienoate (40 g, 0.18 M) and methylene chloride (1 l), at −8° C. under nitrogen and the resulting mixture is stirred for two hours. The precipitate is filtered and the filtrate dried in vacuo to give crude ethyl 4-methyl-8-methylene-4,5-oxido-9-decenoate. This material is dissolved in methanol (200 ml) and the resulting solution is treated with saturated potassium carbonate solution (50 ml) and water (50 ml) and stirred overnight. Most of the methanol is removed in vacuo, the residue is cooled to 0° C. and slowly treated with conc. hydrochloric acid (150 ml). The resulting mixture is extracted with ether (3×350 ml). The combined organic layers are dried (Na$_2$SO$_4$), the solvent is removed in vacuo, and the residue (52 g) is purified by column chromatography on silica gel (400 g) with ether-petroleum ether (4:1) to give 2-(1-hydroxy-4-methylene-5-hexenyl)-2-methyl-5-oxo-tetrahydrofuran as a colorless liquid (22 g, 58%).

IR (neat) 3460, 1770 and 1595 cm$^{-1}$

NMR (CDCl$_3$) δ 1.37 (s, 3H,

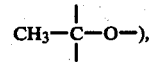

3.78 (bt, 1H,

4.97–6.67 (m, 5H, olefinic protons)

EXAMPLE 4

2-Bromomethyl-5-[2-(2-methyl-5-oxo-tetrahydrofuranyl)]-2-vinyltetrahydrofuran (5a and 5b)

Bromine (15.8 g, 0.1 M) in methylene chloride (10 ml) is added slowly to a mixture of 2-(1-hydroxy-4-methylene-5-hexenyl)-2-methyl-5-oxo-tetrahydrofuran (21.5 g, 0.102 M) and methylene chloride at 0° C. After the addition is complete, the mixture is allowed to warm to room temperature and then stirred overnight. The resultant mixture is treated with water (300 ml). The aqueous phase is extracted with methylene chloride (300 ml), the combined extracts are dried (Na₂SO₄) and the solvent is removed in vacuo to give a dark brown oil (31 g). The oil is purified by column chromatography on silica gel (200 g) with ether-petroleum ether (13:7) to give 2-bromomethyl-5-[2-(2-methyl-5-oxo-tetrahydrofuranyl)]-2-vinyltetrahydrofuran as a light brown oil (12.7, 60% yield).

IR (neat) 1770 cm⁻¹
NMR (CDCl₃) δ 1.40 (s, 3H,

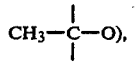

3.4 and 3.41 (both singlets, 2H, -CH₂Br), 5.02–6.2 (m, 3H, olefinic protons)

EXAMPLE 5

2-Bromomethyl-5-[2-(2,5-dihydroxypentanyl)]-2-vinyl tetrahydrofuran (6a and 6b)

A mixture of the isomers of 2-bromomethyl-5-[2-(2-methyl-5-oxo-tetrahydrofuranyl)]-2-vinyltetrahydrofuran (7.4 g, 26 mM) and ether (50 ml) is added slowly to a mixture of lithium aluminum hydride (1 g, 2.7 mM) and ether (300 ml) at 0° C. under nitrogen. After the addition is complete, the mixture is allowed to warm to room temperature and then stirred for two hours. The mixture is then cooled to 0° C. and 5% sodium bicarbonate solution (50 ml) is carefully added. The mixture is filtered through a pad of Celite and the filtrate is dried (Na₂SO₄). The solvent is removed in vacuo to give the crude product (7.3 g). This material is purified by column chromatography on silica gel (200 g) with ethyl acetate-ether (1:4) to give 2-bromomethyl-5-[2-(2,5-dihydroxypentanyl)-2-vinyltetrahydrofuran as a light yellow oil (7.0 g, 94%).

IR (neat) 3460 cm⁻¹

EXAMPLE 6

(1RS,4SR,5RS)-4-(3-Hydroxypropyl)-4-methyl-1-vinyl-3,8-dioxabicyclo[3.2.1]octane (7)

A mixture of the isomers of 2-bromomethyl-5-[2-(2,5-dihydroxypentanyl)]-2-vinyltetrahydrofuran (101 mg, 0.35 mM), sodium hydride (18 mg, 0.72 mM), tetrahydrofuran (10 ml) and hexamethylphosphoramide (1 ml) is heated at 60° C. (bath temperature) for four hours. The resulting mixture is cooled to room temperature, treated with ice-water (10 ml) and dried (Na₂SO₄). The solvent is removed in vacuo to give a pale yellow oil (90 mg). The oil is purified by column chromatography on silica gel (10 g) with ether-petroleum ether (7:3) to give (1RS,4SR,5RS)-4-(3-hydroxypropyl)-4-methyl-1-vinyl-3,8-dioxabicyclo[3.2.1]octane as a colorless liquid (23 mg, 30%).

IR (neat) 3435 cm⁻¹
NMR (CDCl₃) δ 1.38 (s, 3H,

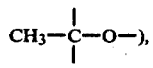

5.06–6.16 (m, 3H, olefinic protons)

EXAMPLE 7

(1RS,4SR,5RS)-4-(3-Methanesulfonyloxypropyl)-4-methyl-1-vinyl-3,8-dioxabicyclo[3.2.1]octane (8)

Methanesulfonyl chloride (200 mg, 2.6 mM) is added slowly to a mixture of (1RS,4SR,5RS)-4-(3-hydroxypropyl)-4-methyl-1-vinyl-3,8-dioxabicyclo[3.2.1]octane (333 mg, 1.6 mM) in methylene chloride (30 ml) and triethylamine (2 ml) at 0° C. and stirred for five minutes. The resulting mixture is treated with methanol (1 ml) and most of the solvent is removed in vacuo. The residue is filtered through a silica gel (20 g) column and washed with ether-petroleum ether (1:1, 300 ml). The solvent is removed in vacuo to give (1RS,4SR,5RS)-4-(3-methanesulfonyloxypropyl)-4-methyl-1-vinyl-3,8-dioxabicyclo[3.2.1]octane (408 mg, 90%) as a colorless oil.

IR (neat) 1650 cm⁻¹
NMR (CDCl₃) δ 1.38 (s, 3H,

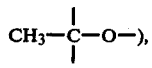

3.10 (s, 3H,

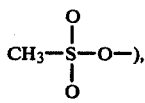

4.20 (t, 2H, J=6 Hz,

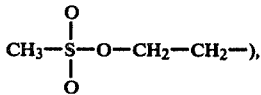

5.12–6.18 (m, 3H, olefinic protons)

EXAMPLE 8

(1RS,4SR,5RS)-4-(3-Methanesulfonyloxypropyl)-4-methyl-3,8-dioxabicyclo[3.2.1]octane-1-ethanol (9)

A mixture of diborane in tetrahydrofuran (1 ml, 1 mM) is added slowly to a mixture of (1RS,4SR,5RS)-4-(3-methanesulfonyloxypropyl)-4-methyl-1-vinyl-3,8-dioxabicyclo[3.2.1]octane (350 mg, 1.2 mM) and tetrahydrofuran (5 ml) at 0° C. under nitrogen and stirred for thirty minutes. The resulting mixture is allowed to warm to room temperature and stirred for an additional two hours. The mixture is cooled to 0° C. and 3 N sodium hydroxide (0.3 ml) is added followed by the addition of 30% hydrogen peroxide (0.3 ml). The resulting mixture is allowed to warm to room temperature and stirred for 2.5 hours. The mixture is then treated with water (10 ml) and extracted with ether (5×20 ml). The combined organic phases are dried (Na₂SO₄) and the solvent is removed in vacuo. The residue is purified by column chromatography on silica gel (30 g) with ether to give (1RS,4SR,5RS)-4-(3-methanesulfonyloxypropyl)-4-methyl-3,8-dioxabicyclo[3.2.1]octane-1-ethanol (275 mg, 80%) as a colorless oil.

IR (neat) 3450 cm⁻¹
NMR (CDCl₃) δ 1.38 (s, 3H,

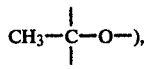

3.02 (s, 3H,

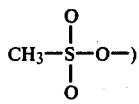

EXAMPLE 9

(1RS,4SR,5RS)-4-(4-Carbomethoxypentyl)-4-methyl-3,8-dioxabicyclo[3.2.1]octane-1-ethanol (11)

A. Methyl-2-lithio propionate is generated from methyl propionate (176 mg, 2 mM) and lithium diisopropylamide (2 mM) in tetrahydrofuran (5 ml) under nitrogen in the usual manner. To this reagent, (1RS,4SR,5RS)-4-(3-methanesulfonyloxypropyl)-4-methyl-3,8-dioxabicyclo[3.2.1]octane-1-ethanol (258 mg, 0.84 mM) in tetrahydrofuran (5 ml) is slowly added at −78° C. and stirred for two hours. The resulting mixture is allowed to warm to room temperature and stirred for an additional hour. This mixture is then poured into saturated aqueous ammonium chloride solution (5 ml) and extracted with ether (5×10 ml). The combined organic layers are dried (Na₂SO₄), the solvent is removed in vacuo and the residue is purified by column chromatography on silica gel (30 g) with ether-petroleum ether (4:1) to give (1RS,4SR,5RS)-4-(4-carbomethoxypentyl)-4-methyl-3,8-dioxabicyclo[3.2.1]octane-1-ethanol (71 mg, 30%) as a colorless oil.

IR (neat) 3450 and 1740 cm⁻¹

NMR (CDCl₃) δ 1.15 (d, J=6 Hz, 3H,

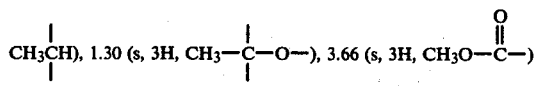

B. Following the procedure for the preparation of (1RS,4SR,5RS)-4-(3-methanesulfonyloxypropyl)-4-methyl-3,8-dioxabicyclo[3.2.1]octane-1-ethanol, but substituting (1RS,4SR,5RS)-4-(4-carbomethoxypentyl)-4-methyl-1-vinyl-3,8-dioxabicyclo[3.2.1]octane for (1RS,4SR,5RS)-4-(3-methanesulfonyloxypropyl)-4-methyl-1-vinyl-3,8-dioxabicyclo[3.2.1]octane, (1RS,4SR,5RS)-4-(4-carbomethoxypentyl)-4-methyl-3,8-dioxabicyclo[3.2.1]octane-1-ethanol is obtained.

EXAMPLE 10

(1RS,4SR,5RS)-4-(4-Carbomethoxypentyl)-4-methyl-1-vinyl-3,8-dioxabicyclo[3.2.1]octane (10)

Following the procedure for the preparation of (1RS,4SR,5RS)-4-(4-carbomethoxypentyl)-4-methyl-3,8-dioxabicyclo[3.2.1]octane-1-ethanol, but substituting (1RS,4SR,5RS)-4-(3-methanesulfonyloxypropyl)-4-methyl-1-vinyl-3,8-dioxabicyclo[3.2.1]octane for (1RS,4SR,5RS)-4-(3-methanesulfonyloxypropyl)-4-methyl-3,8-dioxabicyclo[3.2.1]octane-1-ethanol, (1RS,4SR,5RS)-4-(4-carbomethoxypentyl)-4-methyl-1-vinyl-3,8-dioxabicyclo[3.2.1]octane is obtained.

IR (neat) 1765 and 1640 cm⁻¹

NMR (CDCl₃) δ 1.15 (d, J=6 Hz, 3H,

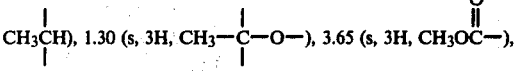

5.0-6.2 (m, 3H, olefinic protons)

EXAMPLE 11

(1RS,4SR,5RS)-4-(4-Carboxypentyl)-4-methyl-3,8-dioxabicyclo[3.2.1]octane-1-ethanol (12)

A mixture of (1RS,4SR,5RS)-4-(4-carbomethoxypentyl)-4-methyl-3,8-dioxabicyclo[3.2.1]octane-1-ethanol (71 mg, 0.24 mM), methanol (3 ml), water (1 ml) and 1 N sodium hydroxide (1 ml) is stirred at room temperature under nitrogen for twenty hours. Most of the methanol is removed in vacuo and the residue is treated with concentrated hydrochloric acid (1 ml) at 0° C. and extracted with ethyl acetate (3×30 ml). The combined organic layers are dried (Na₂SO₄) and evaporated in vacuo to give a colorless oil. This material is filtered through a silica gel column (3 g) and washed with ether (200 ml). The solvent is removed in vacuo to give (1RS,4SR,5RS)-4-(4-carboxypentyl)-4-methyl-3,8-dioxabicyclo[3.2.1]octane-1-ethanol (58 mg, 88%) as a colorless oil.

IR (neat) 3450-2450 (broad), and 1725 cm⁻¹

EXAMPLE 12

(1RS,4SR,5RS)-4-(4,8-Dimethyl-5-oxo-7-nonenyl)-4-methyl-3,8-dioxabicyclo[3.2.1]octane-1-ethanol (13)

A mixture of (1RS,4SR,5RS)-4-(4-carboxypentyl)-4-methyl-3,8-dioxabicyclo[3.2.1]octane-1-ethanol (58 mg, 0.2 mM), lithium hydride (10 mg, 1.25 mM) and ether (5 ml) is stirred at room temperature under nitrogen for two hours. An excess of 3-methyl-2-butenyl lithium is added to this mixture at room temperature. The resulting mixture is stirred for two hours and then treated with 5% sodium bicarbonate solution (5 ml) and extracted with ethyl acetate (3×20 ml). The combined organic layers are dried (Na₂SO₄), evaporated in vacuo and the residue is purified by column chromatography on silica gel (7 g) with ether to give (1RS,4SR,5RS)-4-(4,8-dimethyl-5-oxo-7-nonenyl)-4-methyl-3,8-dioxabicyclo[3.2.1]octane-1-ethanol (13 mg), 25%) as a colorless oil).

IR (neat) 3380 and 1710 cm⁻¹

NMR (CDCl₃) δ 1.30 (s, 3H,

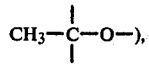

1.63 and 1.75 (both bs, 3H each,

3.11 (d, J=6 Hz, 2H,

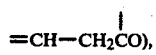

5.28 (bt, J=6 Hz, 1H, >C=C$\underline{H}$-CH₂—)

EXAMPLE 13

(1RS,4SR,5RS)-4-(4,8-Dimethyl-5-hydroxy-7-nonenyl)-4-methyl-3,8-dioxabicyclo[3.2.1]octane-1-acetic acid (14)

A slight excess of Jones reagent is added to a mixture of (1RS,4SR,5RS)-4-(4,8-dimethyl-5-oxo-7-nonenyl)-4-methyl-3,8-dioxabicyclo[3.2.1]octane-1-ethanol (13 mg, 0.04 mM) and acetone (3 ml) at 0° C. under nitrogen for thirty minutes. The resulting mixture is treated with 2-propanol (1 ml) and stirred for ten minutes. The mixture is treated with water (10 ml) and extracted with ether (3×20 ml). The combined organic layers are dried (Na$_2$SO$_4$) and evaporated in vacuo to give crude (1RS,4SR,5RS)-4-(4,8-dimethyl-5-oxo-7-nonenyl)-4-methyl-3,8-dioxabicyclo[3.2.1]octane-1-acetic acid (10 mg) as a yellowish oil. This material is dissolved in methanol (2 ml) and treated with sodium borohydride (50 mg) at 0° C. under nitrogen. After stirring for five minutes, the mixture is allowed to warm to room temperature, acetone (0.5 ml) is added and the resulting mixture is stirred for thirty minutes. Most of the solvent is removed in vacuo, 2 N hydrochloric acid (5 ml) is added and the resulting mixture is extracted with ether (3×10 ml). The combined organic layers are dried (Na$_2$SO$_4$), evaporated in vacuo and the residue is purified by column chromatography on silica gel (5 g) with ether to give (1RS,4SR,5RS)-4-(4,8-dimethyl-5-hydroxy-7-nonenyl)-4-methyl-3,8-dioxabicyclo[3.2.1]octane-1-acetic acid (7 mg) as a colorless oil.

IR (neat): 3460, 1724 cm$^{-1}$

NMR (CDCl$_3$) δ: 0.88 (d, J=7 Hz, 3H,

), 1.31 (s, 3H, CH$_3$C—O—), 1.63 and 1.71 [each s, each 3H, (C$\underline{H}$$_3$)$_2$-C=CH-], 2.60 (s, 2H, -C$\underline{H}$$_2$CO$_2$H), 3.39 and 3.76 (each d, J=11 Hz, 2H,

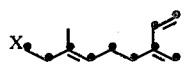

), 5.16 (bt, J=6 Hz, 1H, >C=C$\underline{H}$-CH$_2$—)

We claim:

1. The process for the preparation of a compound of the formula

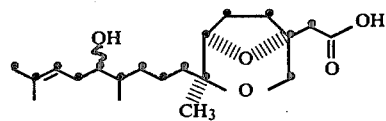

which comprises reacting a compound of the formula

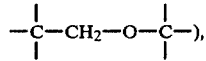

with a compound of the formula

LiCH$_2$CO$_2$C$_2$H$_5$ to form a triene ester of the formula

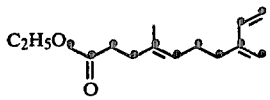

reacting the triene ester with m-chloroperbenzoic acid to form an intermediate of the formula

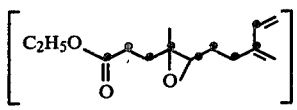

reacting the intermediate first with an aqueous base followed by reaction with acid to form a compound of the formula

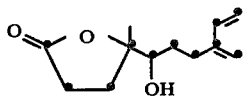

brominating the compound to form epimeric bromides of the formula

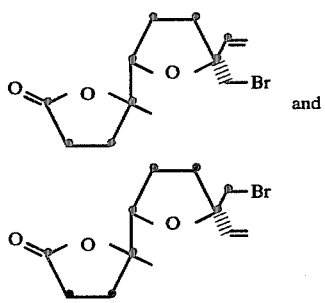

treating the mixture of lactones with lithium aluminum hydride to form a mixture of bromo diols of the formula

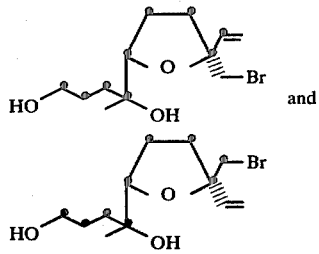

reacting the mixture of bromo diols with sodium hydride to form a mixture of cyclized and uncyclized compounds of the formula

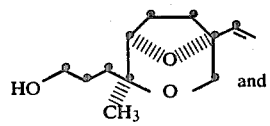

-continued

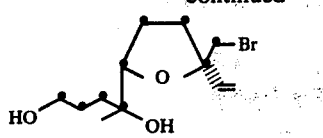

reacting the cyclized compound with methanesulfonyl chloride in the presence of a base to form a compound of the formula

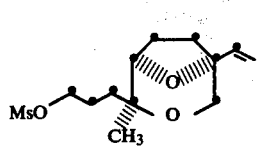

reacting the product formed with diborane followed by oxidation with hydrogen peroxide to give a primary alcohol of the formula

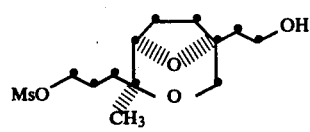

reacting the product with LiCH(CH$_3$)CO$_2$CH$_3$ to form a methyl ester of the formula

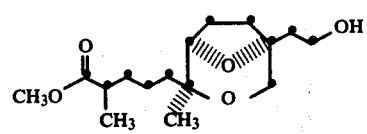

hydrolyzing the ester with base followed by acidification to form an acid of the formula

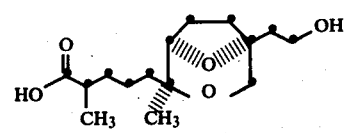

reacting the acid with lithium hydride followed by reaction with 3-methyl-2-butenyl lithium to give a ketone of the formula

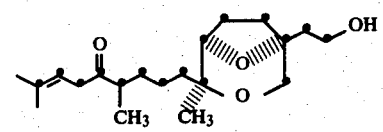

oxidizing the compound followed by reduction with sodium borohydride, wherein X is chloro or bromo, and Ms is a mesyl group.

2. The process of claim 1 wherein the aqueous base is a potassium carbonate solution.

3. The process of claim 1 wherein the hydrolyzing base is sodium hydroxide.

4. The process of claim 1 wherein the oxidizing agent is chromium trioxide-sulfuric acid.

5. The process of claim 1 wherein X is chloro.

6. The process for the preparation of a compound of the formula

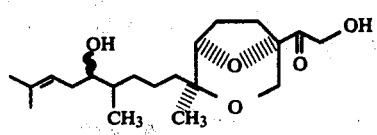

which comprises reacting a compound of the formula

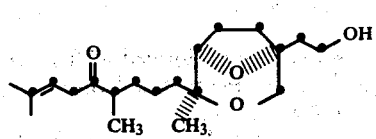

with an oxidizing agent followed by reduction with sodium borohydride.

7. The process of claim 6 wherein the oxidizing agent is chromium trioxide-sulfuric acid.

8. The process for the preparation of a compound of the formula

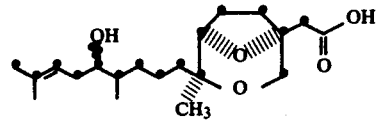

which comprises reacting a compound of the formula

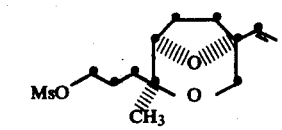

with a compound of the formula

LiCH(CH$_3$)CO$_2$CH$_3$ to form a compound of the formula

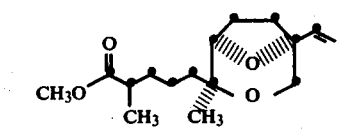

reacting the compound formed with diborane followed by oxidation with hydrogen peroxide to form a compound of the formula

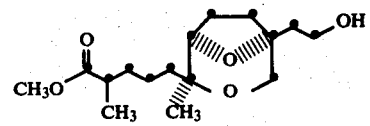

hydrolyzing the ester to form an acid of the formula

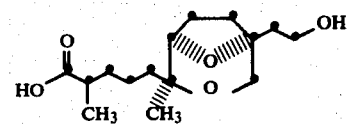

reacting the acid with lithium hydride followed by reaction with 3-methyl-2-butenyl lithium to form a compound of the formula

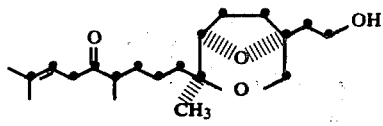

and reacting the keto-alcohol formed with an oxidizing agent followed by reduction with sodium borohydride, wherein Ms is a mesyl group.

9. The process of claim 8 wherein the hydrolyzing agent is sodium hydroxide.

10. The process of claim 8 wherein the oxidizing agent is chromium trioxide-sulfuric acid.

11. A compound of the formula

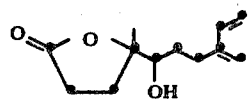

12. A compound of the formula

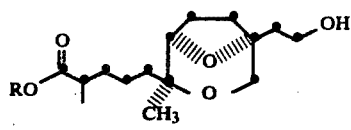

wherein R is hydrogen or methyl.

* * * * *